(12) United States Patent
Wernlund

(10) Patent No.: US 6,229,143 B1
(45) Date of Patent: May 8, 2001

(54) ION MOBILITY SPECTROMETER WITH IMPROVED DRIFT REGION AND METHOD FOR MAKING SAME

(75) Inventor: Roger F. Wernlund, Lake Worth, FL (US)

(73) Assignee: Saes Getters S.p.A., Lainate (IT)

( * ) Notice: Subject to any disclaimer, the term of this patent is extended or adjusted under 35 U.S.C. 154(b) by 0 days.

(21) Appl. No.: 09/657,221

(22) Filed: Sep. 7, 2000

(51) Int. Cl.[7] .................................................. H01J 49/40
(52) U.S. Cl. .............................................................. 250/287
(58) Field of Search ............................................... 250/287

(56) References Cited

U.S. PATENT DOCUMENTS

| | | | |
|---|---|---|---|
| 4,633,083 | * 12/1986 | Knorr et al. | 250/287 |
| 4,855,595 | * 8/1989 | Blanchard | 250/287 |
| 5,244,814 | * 9/1993 | Barbour et al. | 250/287 |
| 5,280,175 | * 1/1994 | Karl | 250/287 |

* cited by examiner

Primary Examiner—Jack Berman
(74) Attorney, Agent, or Firm—Oppenheimer Wolff & Donnelly LLP

(57) ABSTRACT

An ion mobility spectrometer with improved linearity of ion flight path through the non-linear drift region by enhanced electric field due to extensions of guard rings into the non-linear drift region. An improved guard ring with an extension into the non-linear drift region.

14 Claims, 9 Drawing Sheets

ION MOBILITY SPECTROMETER WITH IMPROVED DRIFT REGION AND METHOD FOR MAKING SAME

BACKGROUND

An Ion Mobility Spectrometer (IMS) is a device primarily used for detecting atoms and molecules in a given sample of gas. The theory behind ion mobility spectrometry is that every ionized atom or molecule has a unique size, shape and mass-to-charge ratio, so that when an electric or magnetic force is applied to the ionized atom or molecule, constrained by collisions with the host gas, it will travel at a certain velocity. This velocity can be measured, and thereby the type of atom or molecule can be identified.

The IMS of the prior art is essentially a cylinder operating at atmospheric pressure. Sample gas enters the cylinder at one end, is charged, then is moved through the cylinder by an electric field, and measured at the opposite end. The portion of the cylinder where the gas enters is called the ion molecule reaction region. This section, known as the drift region, is separated from the rest of the cylinder by a control grid. The control grid is a series of parallel wires with alternating charge. The grid thereby keeps most charged particles effectively contained in the ion molecule reaction region until they are lost by contacting a surface.

A series of metal rings along the cylinder, referred to as guard rings, provide a series of electric fields, which create an electrical gradient through the center of the cylinder. This field is what propels the ions though the drift gas within the IMS cylinder when the control grid is opened. The length of time it then takes ion to reach the collector electrode at the opposite end can be precisely measured in terms of milliseconds. Since each ion has a unique size, shape and mass-to-charge ratio, the length of time through the IMS is unique to each particle. A specific compound can be determined in terms of parts per million.

The detection of gasses in the parts per billion, however, is a sensitive process. The less concentrated a particle is, the harder it its to detect over the background signals, referred to as noise. Also, if a particular ionized atom or ionized molecule has a flight time through the IMS that is similar to a more abundant gas, its signal can be lost if the resolution of the system is not accurate enough.

The way to correct this problem is to repeat the measuring process tens, hundreds or even thousands of times, and is called signal averaging. By doing this a signal can become readily apparent over background noise, even at very low concentrations. However, if the system is not accurate enough, a weak signal can still get lost next to a strong one. Further, it is not always practical to repeat the detection process hundreds or thousands of times, such as when testing for toxic gasses in real time.

Therefore anything that can help to improve signal to noise ratio and signal resolution would be useful and needed.

One cause of signal deterioration is the guard rings themselves. The guard rings form an inner space in which the ions pass. The middle of the inner space is referred to as the linear region. This region has a diameter approximately half that of the inner space the guard rings form. In this space the ions travel in a linear path. As the flight of an ion starts closer to the guard rings, halfway between the guard rings and the centerline of the cylinder, the ions start to drift more towards the edges. This less linear electric field region is caused by the proximity of the ions to the guard rings. The closer the ion starts to the guard rings, the greater the sidewise drift and the longer the path length. This will cause signals to be less sharp as some of the measured ions and molecules are taking longer to reach the collector electrode as they travel at an angle rather than a straight line. Further, some of the ions drift to such an extent that they hit the grid mounting device or other obstruction and are totally lost for signal measuring purposes.

Attempts have been made to correct this problem. One such solution is to block, or otherwise not read, the ions that are not traveling in the linear zone. This ensures a more uniform flight time of the measured ions, and creates a sharper peak. However, a large number of the ions are blocked from being read by the collector, and this lowers the signal to noise ratio, since the area of the outer less linear drift region is substantially larger than the surface area of the inner linear drift region.

What is needed is a way of improving the electric field linearity so that like ions passing through all portions of the drift region exhibit the same time of flight and thereby the signal resolution can be improved without sacrificing the signal to noise ratio.

SUMMARY OF THE INVENTION

It is an object of the present invention to provide an IMS with improved linearity of ions traveling in the drift region in order to improve resolution.

The guard rings of an IMS provide the electric field, which propel the ions through the IMS. Proximity of ions to the guard rings, however, causes them to deviate from their linear path in the direction of the IMS wall. In one embodiment of the invention, a narrow extension of the guard rings extends from at least one guard ring toward the centerline of the IMS. This has the appearance of a washer inserted into the middle of a guard ring, the washer having a smaller inner diameter than the guard ring.

In another embodiment of the current invention, a narrow protrusion extends from every guard ring toward the centerline of the IMS. In a further refinement of this embodiment, all of the extensions are of the same length.

In one embodiment, at least two guard rings have extension towards the centerline of the IMS, one of them being the guard ring closest to the final screen grid and the collector. In this embodiment, the extension of the guard ring closest to the screen grid has the longest extension. In a further refinement of this embodiment, the each guard ring has an extension towards the centerline, with the shortest extension being the guard ring closest to the control grid, and each successive guard ring having a longer extension, as it gets closer to the grid collector.

In yet another embodiment of the invention, the extension of the guard ring into drift region is accomplished by a series of protrusions, like spikes, rather than a uniform disc.

DETAILED DESCRIPTION OF THE DRAWINGS

Figure 1:
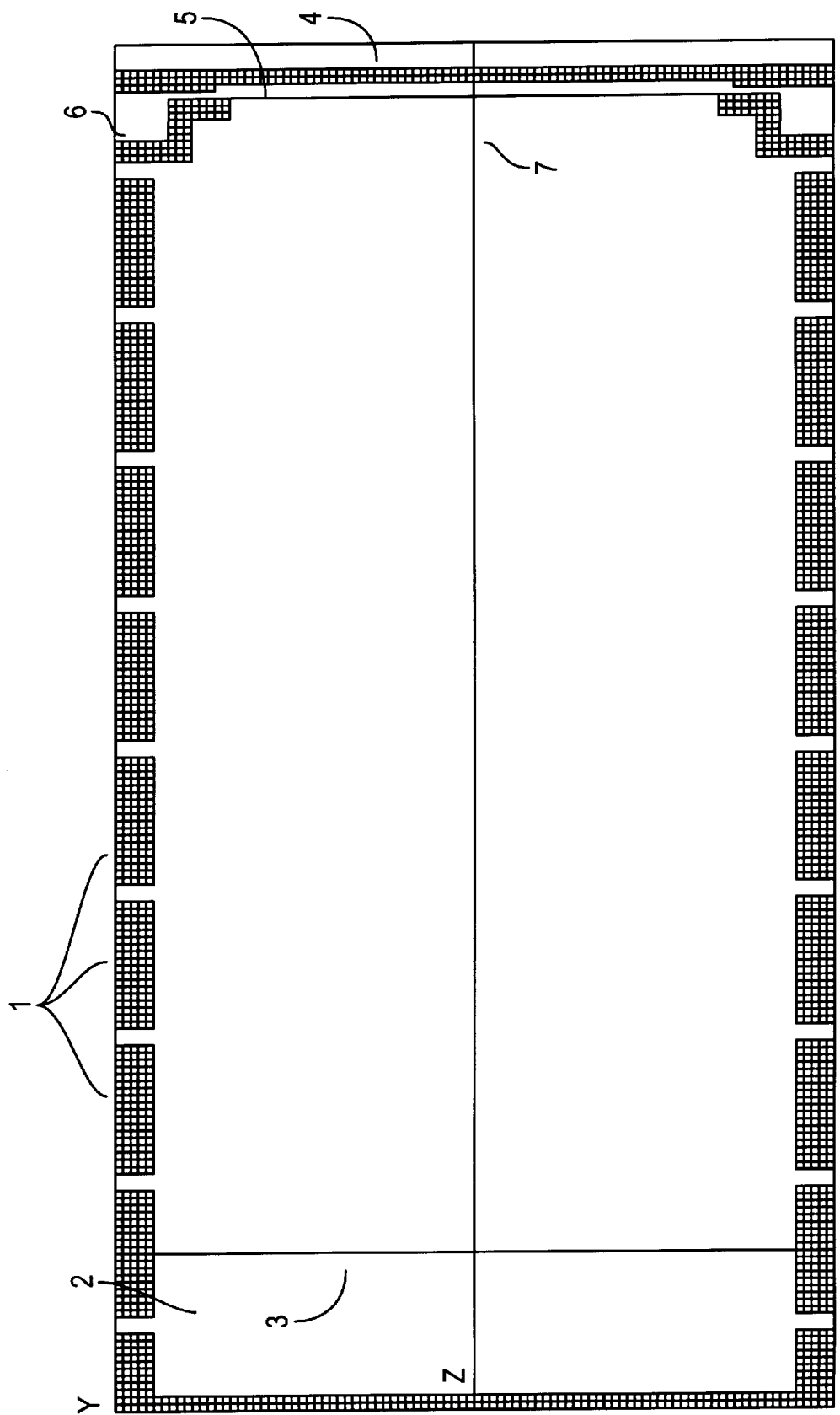
FIG. 1 shows a linear cross section of an IMS as per the prior art.

FIG. 1 shows a linear cross section of a typical IMS as per the prior art. Essentially, an IMS is a hollow cylinder formed by stacking multiple rings, referred to as guard rings 1. These guard rings charged at various levels so that they provide an electrical field gradient through the center of the IMS. The guard rings are typically made out of stainless steel, and are separated from each other by some insulating means. Small beads of saphire are good for this purpose. The series of guard rings are then sheathed to form the main body of the IMS.

One end of the cylinder thus formed is the ion molecule reaction region 2, in which a desired gas sample is injected and the atoms and molecules thereof are charged. The ion molecule reaction region is separated from the rest of the cylinder by a control grid 3, which is made up of a series of closely spaced parallel wires with an alternating charge. This control grid effectively keeps charged particles contained in the ion molecule reaction region 2 until they are released in microsecond intervals.

The charged atoms and molecules, ions, are then pulled through the IMS by the electrical field gradient supplied by the guard rings 1. Milliseconds later they reach the ion collector 4, which registers their impact, thereby measuring the time of flight of the ion through the IMS. Also contained in the IMS in close proximity to the ion collector 4, often no more than half a millimeter apart, is the screen grid 5, which is mounted on the screen grid mounting device 6. The ions pass through the screen grid right before impacting with the ion collector 4.

Figure 2A:
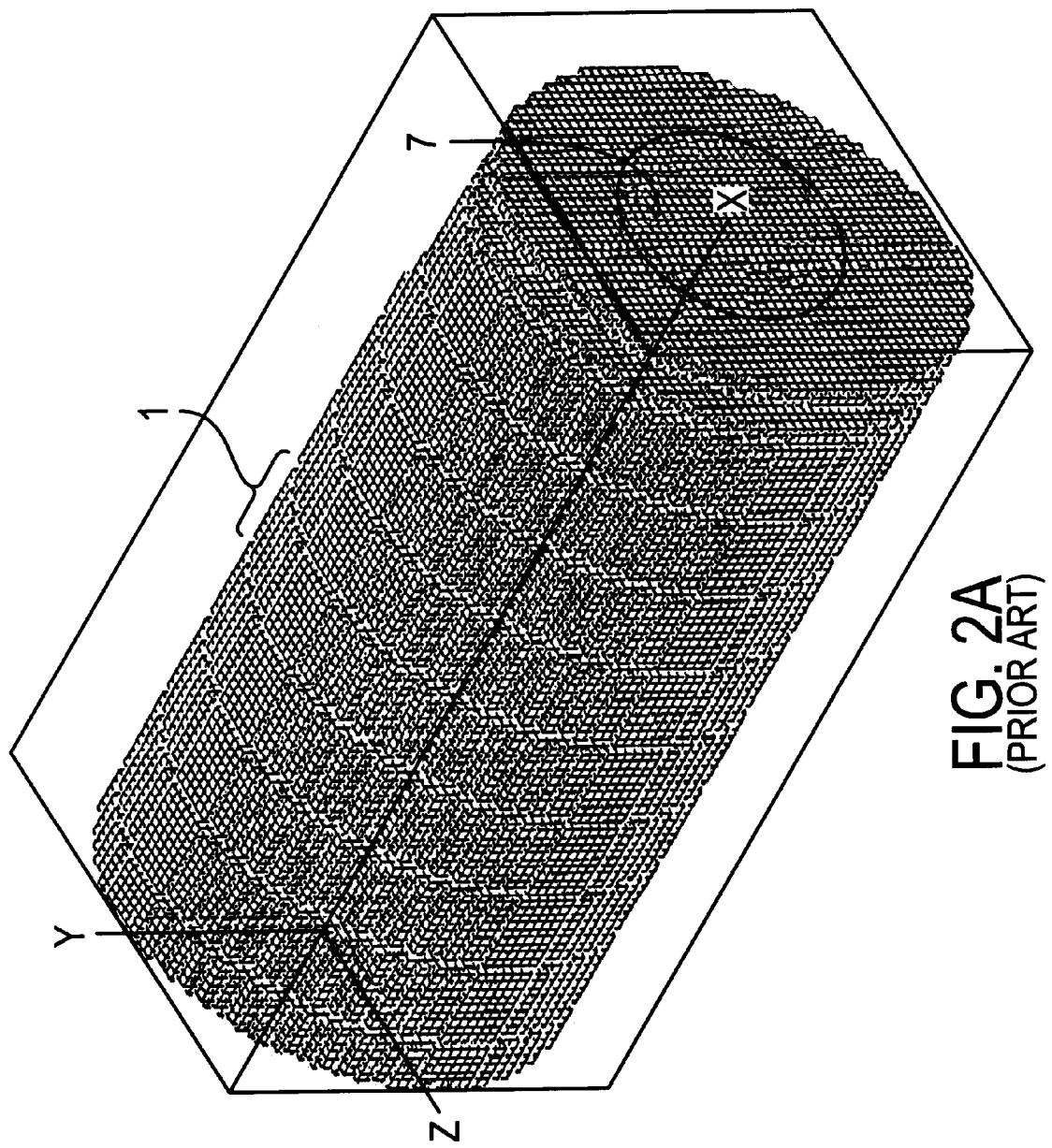
FIGS. 2A and 2B shows the three-dimensional shape of the external region of an IMS.
Figure 2B:
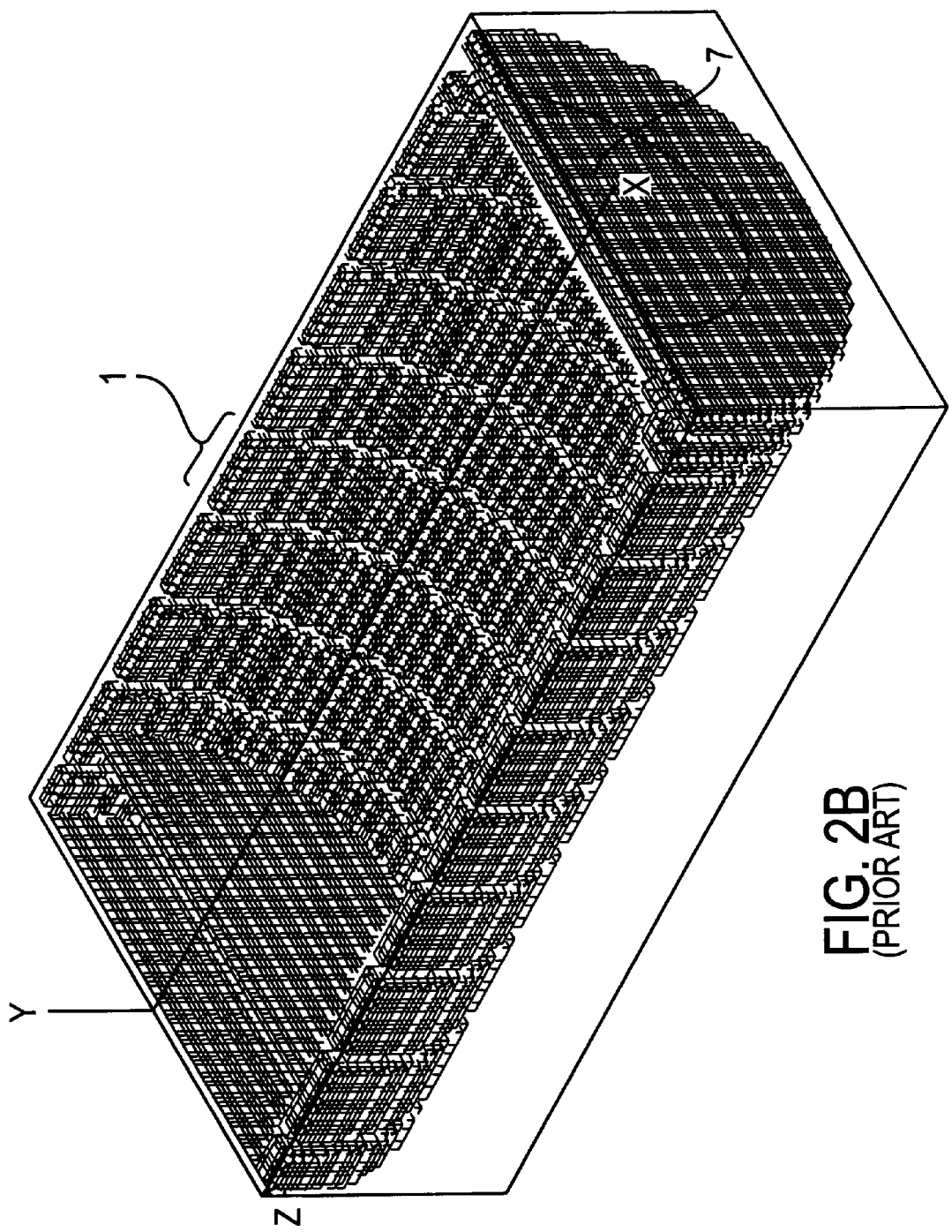

The centerline 7 is a theoretical line that passes through the exact center of the IMS. The centerline 7 is shown again in FIG. 2A, which is a three-dimensional rendering of the IMS. Originally the internal space of an time of flight mass spectrometer was evacuated so that ions would travel through a vacuum. However, the IMS is filled with a uniform gas at atmospheric pressure. The flight times of ions through a gas filled IMS are different than those through a vacuum, but the fingerprint is still unique, and concentrations can still be measured accurately in this manner without the excess difficulty of maintaining a vacuum. FIG. 2B is a cut-away of the object shown in FIG. 2A.

Figure 3:
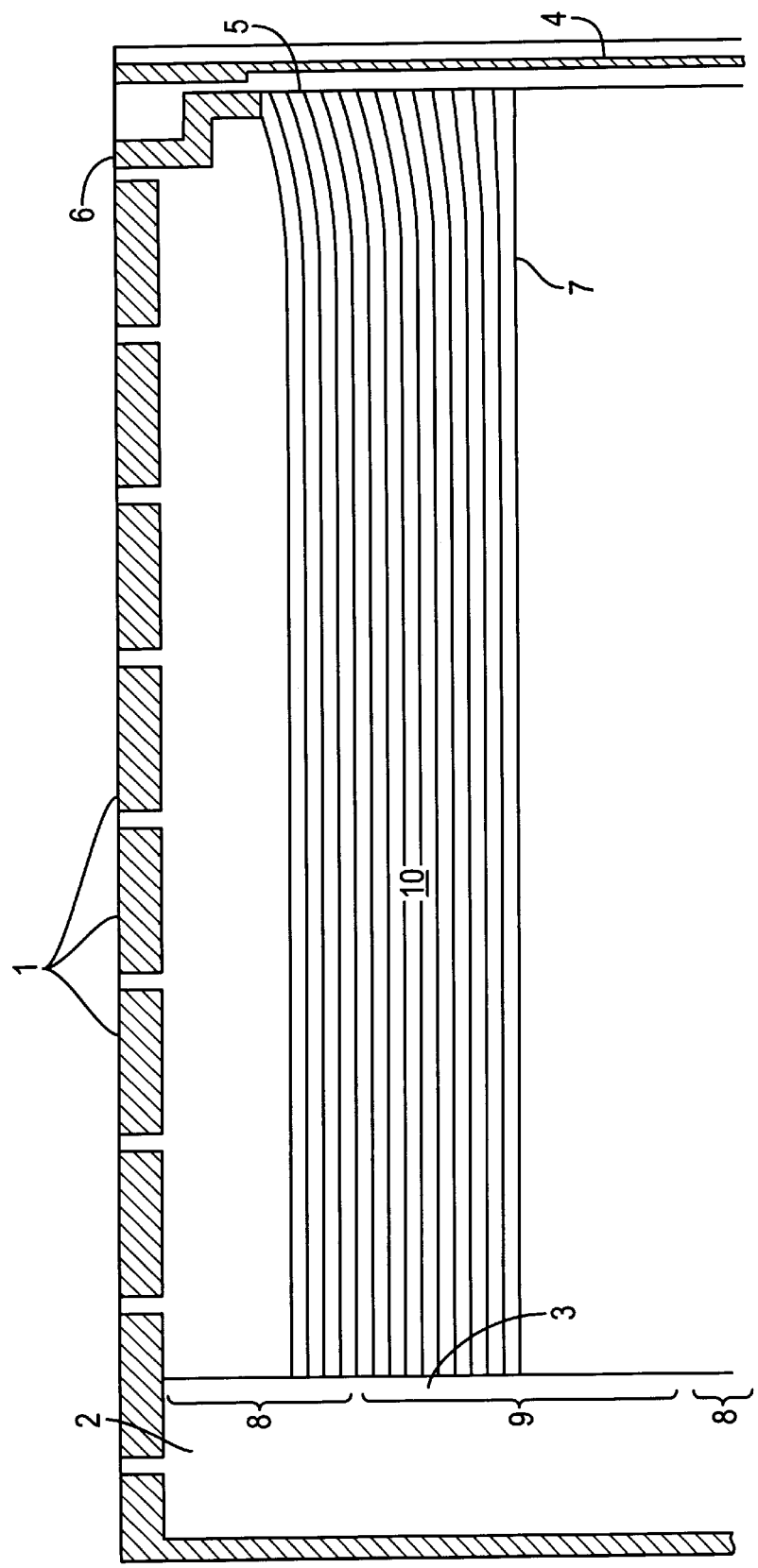
FIG. 3 shows a partial linear cross section of an IMS as per the prior art with the drift region and linear region indicated, as well as examples of the flight path of ions in these regions.

FIG. 3 shows the upper portion of the linear cross section of FIG. 1 along with an indication of the drift region 8, linear region 9 (due to the more linear electric field) and the flight paths of various ions 10 from regular intervals out from the centerline 7. The drift region 8, due to the less linear electric field, begins approximately halfway between the centerline 7 and the guard rings 1. The closer an ion is to the guard rings 1 when it begins its flight, the greater the drift the ion has towards the outer edge of the IMS. This drift causes an ion to take longer in its path though the IMS, causing the resulting signal peak to loose definition. Also, some of the ions drift so much as to collide with the grid screen mounting device 6, so that their signal is totally lost. This causes a lowering of the signal to noise ratio.

Figure 4:
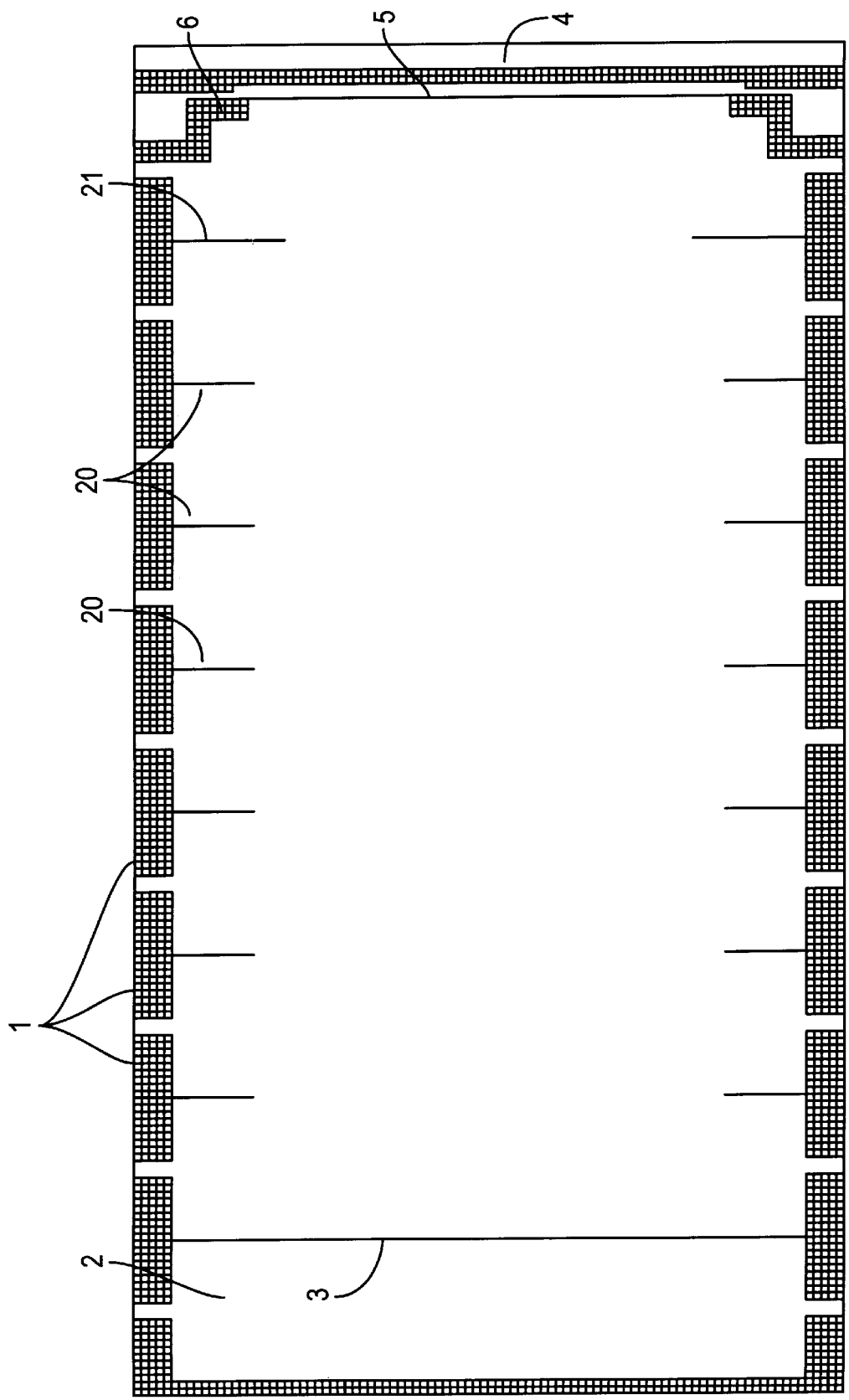
FIG. 4 shows a linear cross section of an IMS bearing one embodiment of the current invention.

FIG. 4 shows one embodiment of the current invention. Extensions of the guard rings 20 enter the drift region (not labeled) and improve the electric field in this region without impeding the flight path of the ions. In this figure all of the guard rings have extensions (except for the guard ring that joins with the control grid). The extension closest to the collector 21 extends the furthest into the drift region. Variations of this embodiment may not have extensions in all of the guard rings, and the extensions may be or uniform or ascending length.

Figure 5:
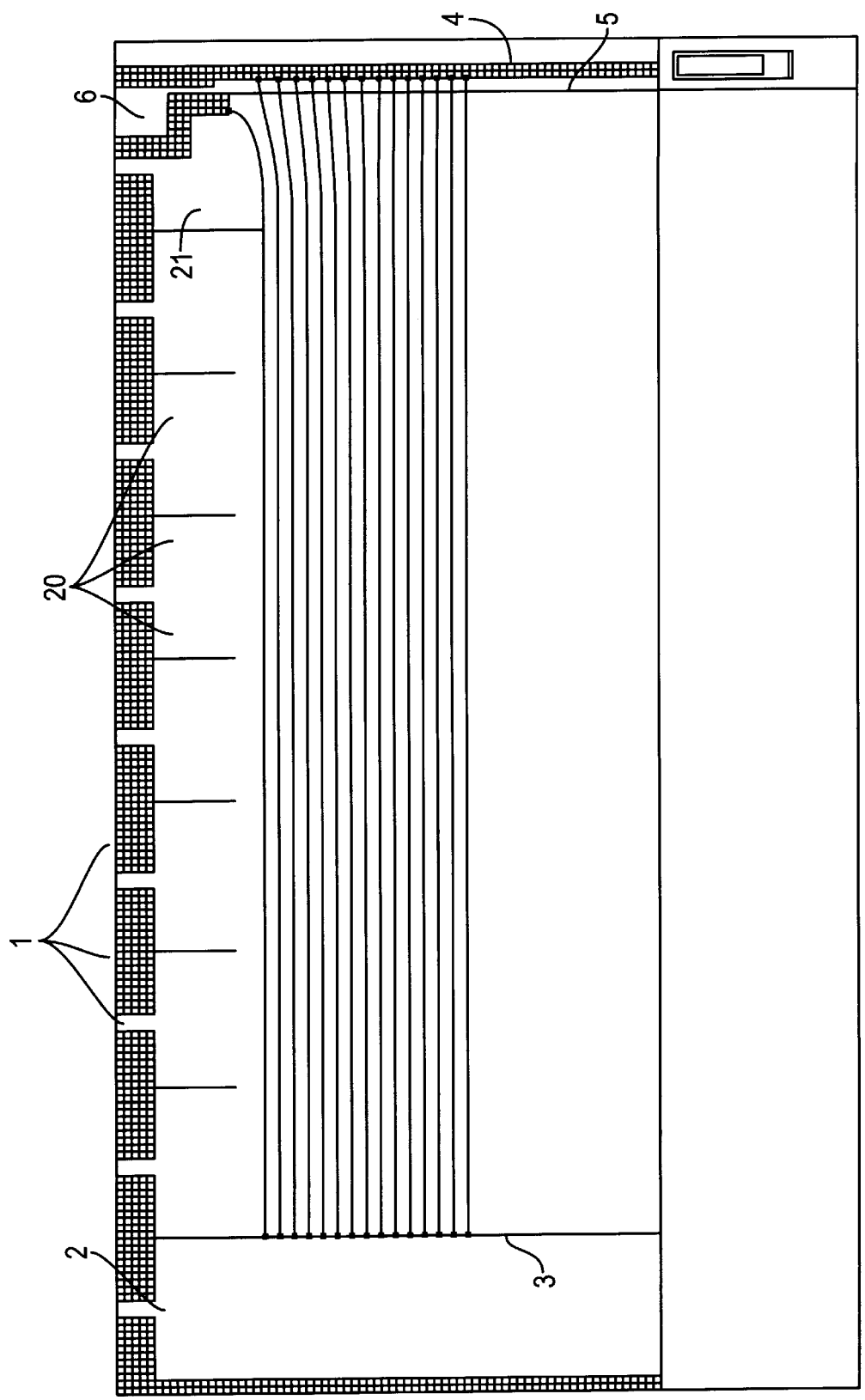
FIG. 5 shows a partial linear cross section of an IMS bearing one embodiment of the current invention with the drift region and linear region indicated, as well as examples of the flight path of ions in these regions.
Figure 6A:
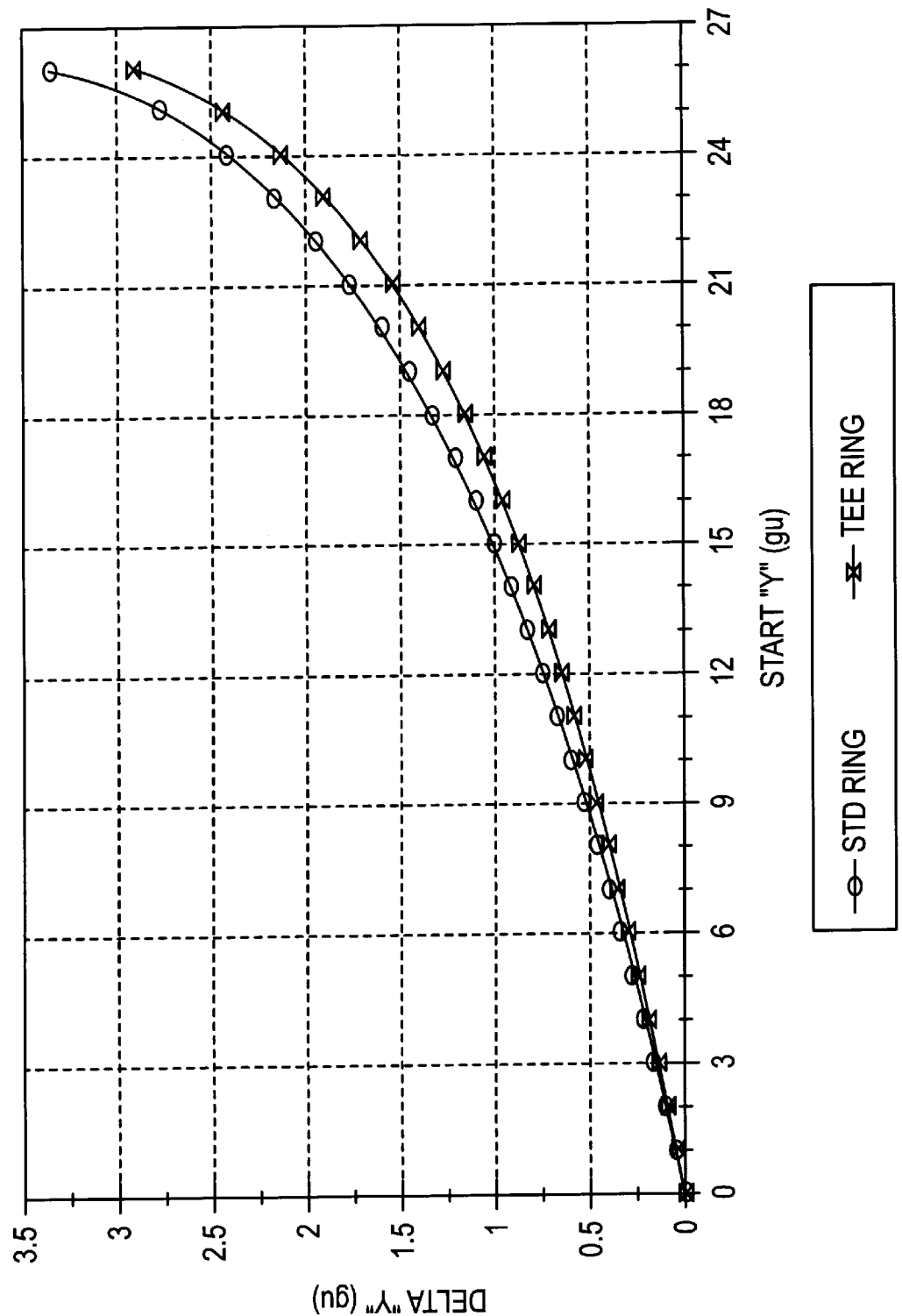
FIGS. 6A 6B shows graphs contrasting the time of flight of example ions in an IMS as per the prior art versus the current invention.
Figure 6B:
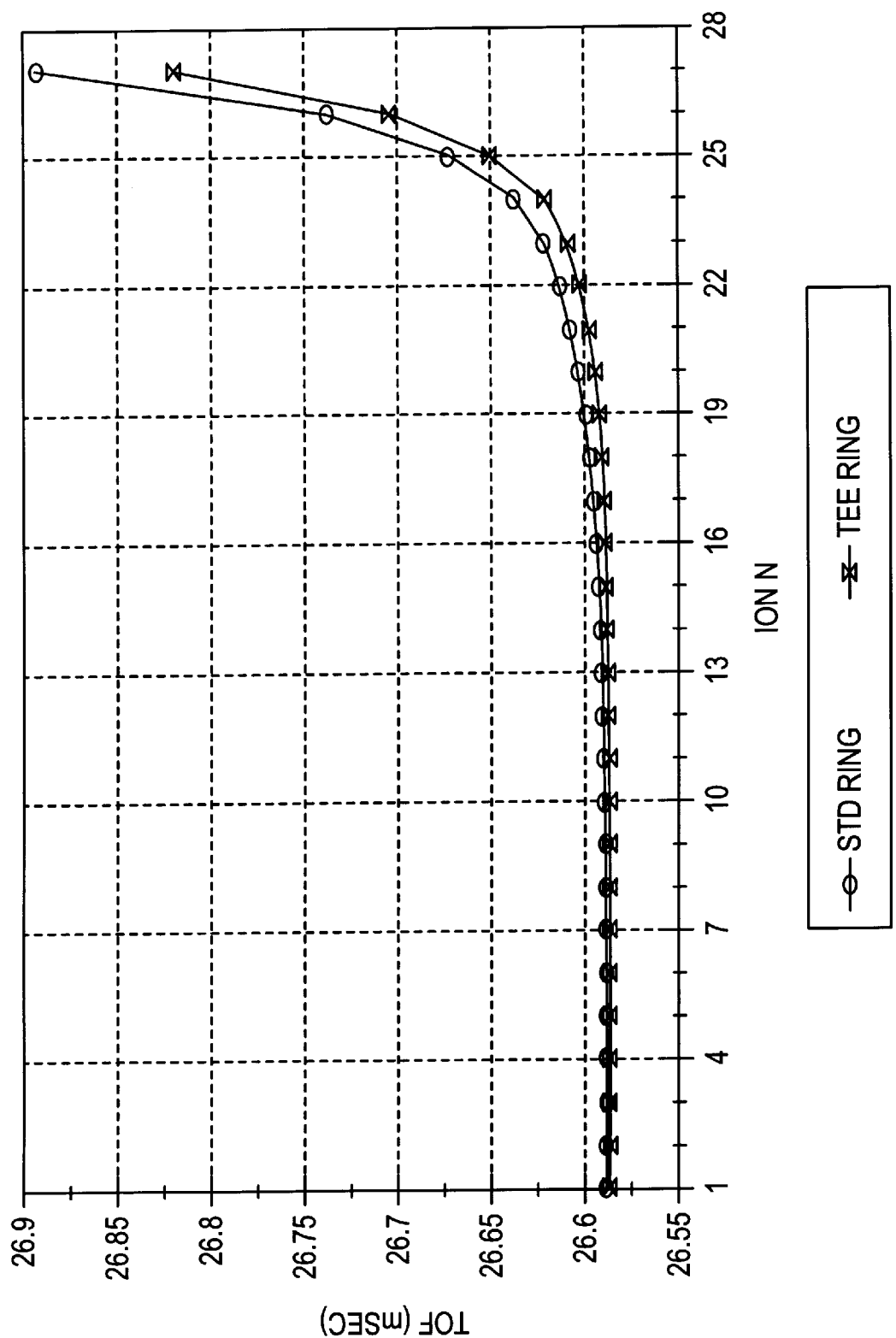

FIG. 5 shows the flight path of example ions in the improved IMS. Ions in the drift region still experience some drift, but as shown in FIG. 6A, a projected improvement of up to 20% can be expected in some instances. In FIG. 6A, delta Y represents a the drift away from center and the ion number is a theoretical ion sampled at a consistent interval out from the centerline, with ion 1 being at the centerline and ion 28 being the furthest measurable ion out. The top graph in circles represents ions in an IMS as per the prior art, and the lower graph, with improved delta Y, represents ions traveling through an IMS as per the embodiment of the invention shown in FIG. 6A. The further the ions are from the centerline the greater the improvement on the delta Y is. It is important to consider here that the number of actual ions represented by the ions in FIG. 6A go up as the distance out from the centerline is increased. FIG. 6B shows a similar graph where the drift is shown in time of flight (TOF).

Figure 7:
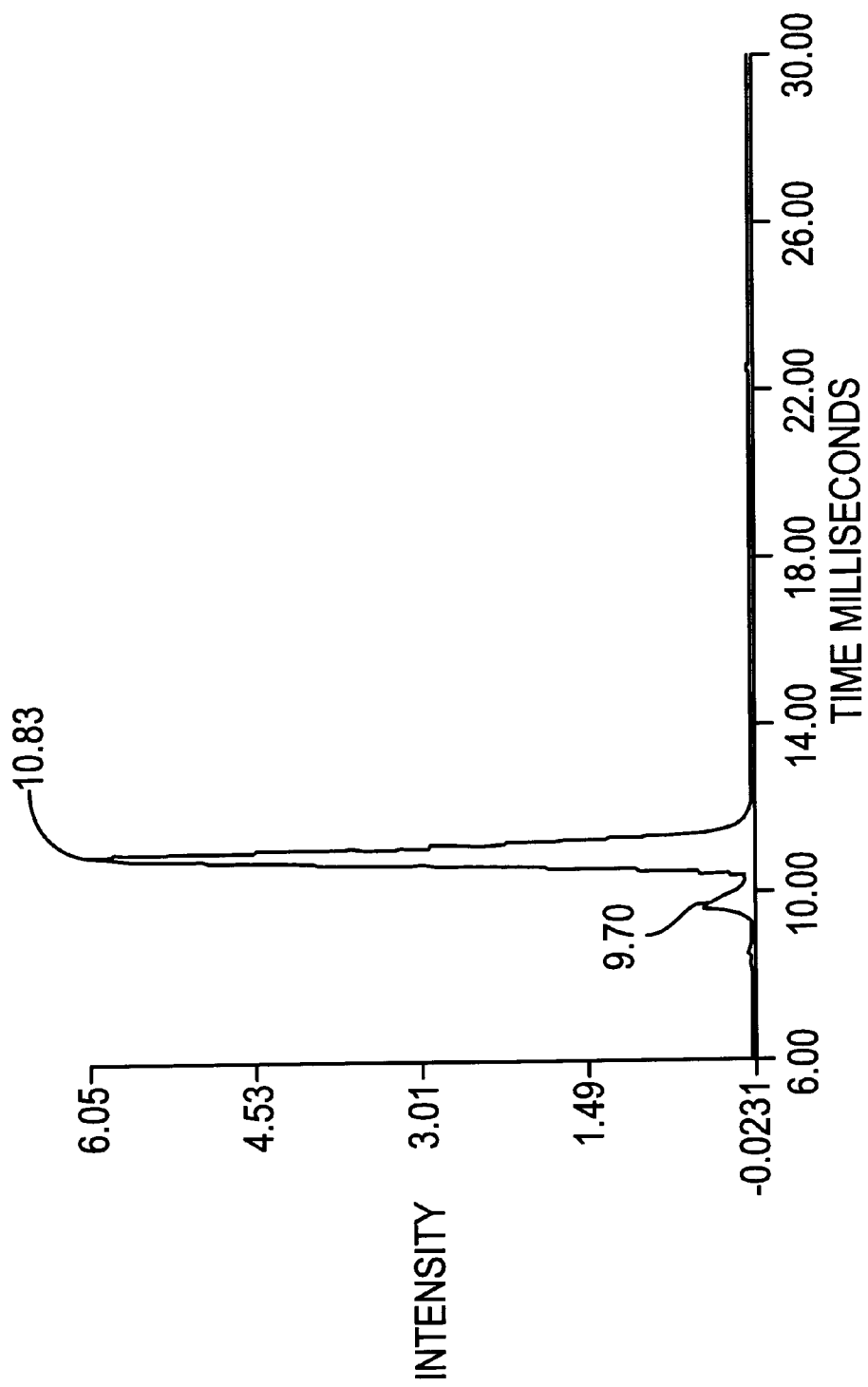
FIG. 7 shows an example of a readout of an IMS.

FIG. 7 is an example of a signal readout taken by an IMS. This example graph shows how a smaller peak can be lost next to a larger peak if the signals are not sharp enough.

What is claimed is:

1. An ion mobility spectrometer comprising:

a series of metal rings, each of said metal rings having an inner and outer diameter and a width, said metal rings forming a cylinder with two ends and a center region, said series of metal rings providing an electric field gradient through said center region;

a control grid at one end of said series of metal rings;

an ion collector at an end of said series of metal rings opposite said control grid; and at least one second metal ring, having an inner and outer diameter and a width, is located mid way through at least one of said metal rings;

wherein said second metal ring has a smaller inner diameter and smaller width than said metal rings, whereby said second metal ring extends further into said center region than said metal rings.

2. The ion mobility spectrometer according to claim 1 wherein a said second metal ring is located mid way through at least two of said metal rings.

3. The ion mobility spectrometer according to claim 2 wherein said second metal rings have different inner diameters.

4. The ion mobility spectrometer according to claim 2 wherein said second metal rings have different widths.

5. The ion mobility spectrometer according to claim 1 wherein a said second metal ring is located mid way through all of said metal rings.

6. The ion mobility spectrometer according to claim 5 wherein said second metal rings have different inner diameters.

7. The ion mobility spectrometer according to claim 5 wherein said second metal rings have different widths.

8. The ion mobility spectrometer according to claim 1 wherein said second metal ring has an inner diameter that forms a star rather than a circle, whereby a series of projections extends into said center region rather than a uniform circle.

9. The ion mobility spectrometer according to claim 6 wherein said second metal ring closest to said screen grid has the smallest inner diameter of all of said second metal rings.

10. The ion mobility spectrometer according to claim 2 wherein one of said second metal rings is midway through the metal ring closest to said ion collector.

11. The ion mobility spectrometer according to claim 6 wherein said second metal ring closest to said control grid has the largest inner diameter of all of said metal rings, and the diameter of each of said second metal rings is smaller the closer said second metal ring is to said ion collector.

12. A method for making an ion mobility spectrometer consisting of the steps of forming:

a series of metal rings, each of said metal rings having an inner and outer diameter and a width, said metal rings form a cylinder with two ends and a center region, said series of metal rings provide an electric field gradient through said center region;

a control grid at one end of said series of metal rings;

a screen grid at an end of said series of metal rings opposite said control grid;

an ion collector at the same end as said screen grid; and at least one second metal ring, having an inner and outer diameter and a width, is located mid way through at least one of said metal rings;

wherein said second metal ring has a smaller inner diameter and smaller width than said metal rings, whereby said second metal ring extends further into said center region than said metal rings.

13. A guard ring having a ring shape, a width, a center, an inner diameter and an outer diameter, wherein the improvement comprises an extension of the guard ring from the inner diameter to the center having a width less than said guard ring, wherein a second inner diameter is formed having a diameter smaller then the inner diameter of said guard ring, whereby the extension has the appearance of a washer inserted linearly into the middle of said guard ring.

14. A guard ring having a ring shape, a width, a center, an inner diameter and an outer diameter, wherein the improvement comprises a series of projections from the inner diameter of said guard ring towards the center of said guard ring, wherein the projections do not fully extend towards the center.

* * * * *